US011752341B2

(12) United States Patent
Libbus et al.

(10) Patent No.: US 11,752,341 B2
(45) Date of Patent: Sep. 12, 2023

(54) DISPLAY SIGNAL TO ASSESS AUTONOMIC RESPONSE TO VAGUS NERVE STIMULATION TREATMENT

(71) Applicant: LivaNova USA, Inc., Houston, TX (US)

(72) Inventors: Imad Libbus, St. Paul, MN (US); Scott R. Stubbs, Maple Grove, MN (US); Scott Mazar, Woodbury, MN (US); Bruce KenKnight, Maple Grove, MN (US); Badri Amurthur, Los Gatos, CA (US)

(73) Assignee: LivaNova USA, Inc., Houston, TX (US)

( * ) Notice: Subject to any disclaimer, the term of this patent is extended or adjusted under 35 U.S.C. 154(b) by 0 days.

(21) Appl. No.: 17/054,996

(22) PCT Filed: May 13, 2019

(86) PCT No.: PCT/US2019/031992
§ 371 (c)(1),
(2) Date: Nov. 12, 2020

(87) PCT Pub. No.: WO2019/222087
PCT Pub. Date: Nov. 21, 2019

(65) Prior Publication Data
US 2021/0213291 A1 Jul. 15, 2021

Related U.S. Application Data

(60) Provisional application No. 62/672,011, filed on May 15, 2018.

(51) Int. Cl.
*A61N 1/36* (2006.01)
*A61N 1/372* (2006.01)

(52) U.S. Cl.
CPC ...... *A61N 1/36114* (2013.01); *A61N 1/36139* (2013.01); *A61N 1/36175* (2013.01); *A61N 1/37247* (2013.01)

(58) Field of Classification Search
CPC ............ A61N 1/36114; A61N 1/36139; A61N 1/36175; A61N 1/36178; A61N 1/37247
(Continued)

(56) References Cited

U.S. PATENT DOCUMENTS 7,103,414 B1 9/2006 Poore et al.
8,239,028 B2 8/2012 Scott
(Continued)

FOREIGN PATENT DOCUMENTS

| CN | 105009315 A | 10/2015 |
| WO | WO-2007/115118 A1 | 10/2007 |
| WO | WO-2013/086163 A1 | 6/2013 |

OTHER PUBLICATIONS

International Search Report and Written Opinion for PCT/US2019/031992 dated Jul. 22, 2019. 9 pages.
(Continued)

*Primary Examiner* — Mallika D Fairchild
*Assistant Examiner* — Shreya Anjaria
(74) *Attorney, Agent, or Firm* — Foley & Lardner LLP

(57) ABSTRACT

An assessment system is provided for vagus nerve stimulation therapy treatment for congestive heart failure in a subject. The assessment system includes a first interface configured to communicate with a device that delivers a stimulation signal to a vagus nerve of the subject, a second interface configured to capture heart electrical activity of the subject in response to the stimulation signal, and a processor and a non-transitory computer readable memory storing instructions that, when executed by the processor, cause the assessment system to determine and display heart rate
(Continued)

dynamics and display a digital ECG signal in real-time in response to the stimulation signal.

20 Claims, 10 Drawing Sheets

(58) Field of Classification Search
USPC .......................................................... 607/25
See application file for complete search history.

(56) References Cited

U.S. PATENT DOCUMENTS

| | | |
|---|---|---|
| 9,079,034 B2 | 7/2015 | Milbocker |
| 2003/0040774 A1 | 2/2003 | Terry et al. |
| 2005/0182755 A1 | 8/2005 | Tran |
| 2006/0241725 A1 | 10/2006 | Libbus et al. |
| 2007/0027496 A1 | 2/2007 | Parnis et al. |
| 2007/0255330 A1 | 11/2007 | Lee et al. |
| 2008/0118126 A1* | 5/2008 | Sakaguchi ............. A61B 6/032 382/128 |
| 2008/0140141 A1 | 6/2008 | Ben-David et al. |
| 2010/0191304 A1 | 7/2010 | Scott |
| 2010/0274308 A1 | 10/2010 | Scott |
| 2012/0083700 A1 | 4/2012 | Osorio |
| 2012/0185007 A1 | 7/2012 | Ziegler et al. |
| 2013/0158618 A1 | 6/2013 | Libbus et al. |
| 2013/0253616 A1 | 9/2013 | Libbus et al. |
| 2014/0364921 A1 | 12/2014 | Legay et al. |
| 2015/0073237 A1 | 3/2015 | Osorio |
| 2015/0306395 A1 | 10/2015 | Libbus et al. |
| 2015/0374983 A1 | 12/2015 | Simon et al. |
| 2016/0038754 A1 | 2/2016 | Adjouadi et al. |
| 2016/0101289 A1 | 4/2016 | Stolen et al. |
| 2016/0158554 A1* | 6/2016 | Graig ................. A61N 1/36064 607/62 |
| 2016/0339242 A1 | 11/2016 | Cook et al. |
| 2019/0247664 A1 | 8/2019 | Irazoqui et al. |
| 2020/0345251 A1 | 11/2020 | Falk et al. |

OTHER PUBLICATIONS

EP Supplementary Search Report on EP Appl. Ser. No. 19803728.5 dated Jan. 25, 2022 (10 pages).
CN First Office Action for CN Appl. Ser. No. CN201980003312.9 dated Jun. 10, 2020 (11 pages).
CN Second office action on CN Appl. Ser No. 201980003312.9 dated Dec. 30, 2020 (8 pages).
EP Office Action on EP Appl. Ser. No. 19802790.6 dated Feb. 17, 2022 (1 page).
EP Search Report on EP Appl. Ser. No. 198202790.6 dated Jan. 31, 2022 (10 pages).
EP Search Report on EP Appl. Ser. No. 19803063.7 dated Jan. 28, 2022 (10 pages).
EP Search Report on EP Appl. Ser. No. 19803136.1 dated Jan. 31, 2022 (5 pages).
International Search Report and Written Opinion on PCT Appl. Ser. No. PCT/US2019/031991 dated Jul. 29, 2019 (10 pages).
International Search Report and Written opinion on PCT Appl. Ser. No. PCT/US2019/031994 dated Jul. 24, 2019 (9 pages).
International Search Report and Written Opinion on PCT Appl. Ser. No. PCT/US2019/031997 dated Jul. 26, 2019 (10 pages).
Libbus et al., "Quantitative evaluation of heartbeat interval time series using Poincare analysis reveals distinct patterns of heart rate dynamics during cycles of vagus nerve stimulation in patients with heart failure," Journal of Electrocardiology, Jun. 8, 2017, vol. 50, No. 6 (pp. 898-903) p. 900, left-hand column; figure 2* .

* cited by examiner

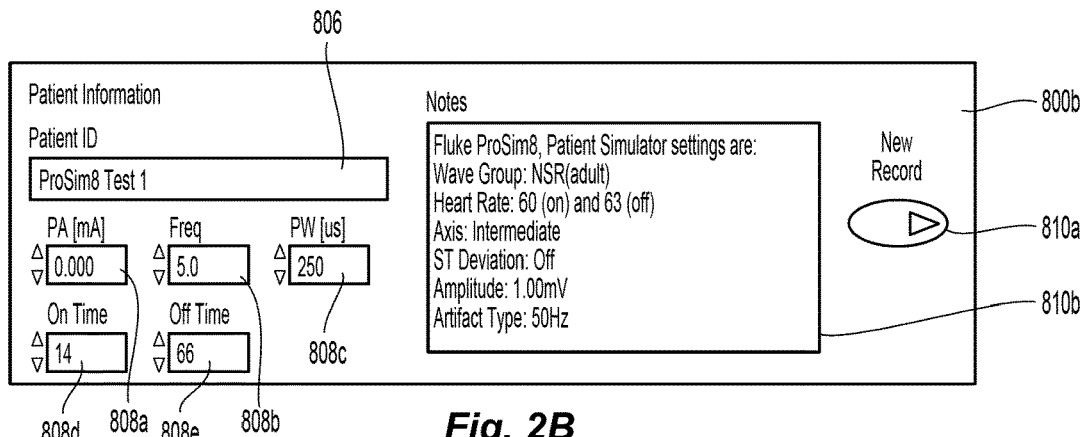
*Fig. 2B*
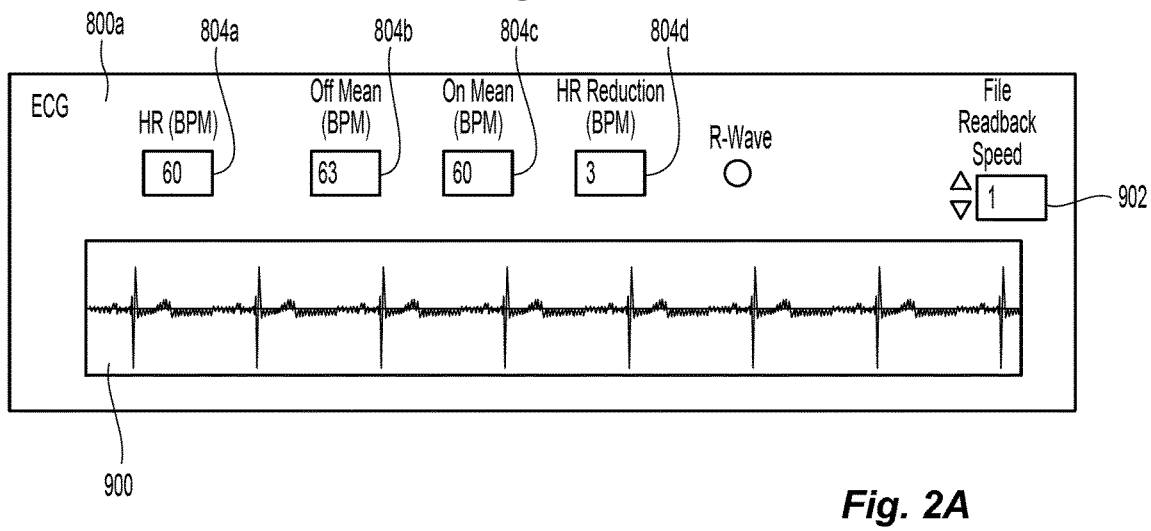
*Fig. 2A*
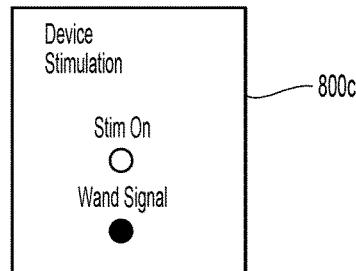
*Fig. 2C*
*Fig. 2D*

US 11,752,341 B2

DISPLAY SIGNAL TO ASSESS AUTONOMIC RESPONSE TO VAGUS NERVE STIMULATION TREATMENT

CROSS-REFERENCE TO RELATED PATENT APPLICATIONS

This application is a U.S. National Stage Application of PCT/US2019/031992, filed May 13, 2019, which claims the benefit of and priority to U.S. Provisional Patent Application No. 62/672,011, entitled "SYSTEMS AND METHODS TO DISPLAY HEART RATE DYNAMICS AND ECG RESPONSE SIGNAL TO ASSESS AUTONOMIC ENGAGEMENT RESPONSE TO VAGUS NERVE STIMULATION IN TREATMENT OF CONGESTIVE HEART FAILURE," filed May 15, 2018, which is incorporated herein by reference in its entirety.

TECHNICAL FIELD

The present disclosure relates generally to systems and methods of neurostimulation therapy and in particular, to systems and methods using dynamic graphical displays for assessing autonomic response to vagus nerve stimulation therapy in the treatment of congestive heart failure.

BACKGROUND

Autonomic regulation neurostimulation therapy delivered by vagus nerve stimulation ("VNS") is a treatment for congestive heart failure. VNS therapy commonly requires implantation of a neurostimulator, which, when activated, applies or delivers a stimulation signal to the vagus nerve of a patient. A vagus nerve stimulation signal is typically a periodic current pulse signal defined by an output current amplitude or intensity. Following implantation and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under the control of a physician with the patient given time between successive increases in VNS therapy intensity to adapt to the new intensity. As stimulation is chronically applied at each new intensity level, the patient's side effect threshold gradually increases, allowing tor an increase in intensity during subsequent titration sessions.

SUMMARY

Embodiments of systems and methods are provided for monitoring and displaying physiological response to neurostimulation therapy. One embodiment relates to an assessment system for vagus nerve stimulation therapy treatment for congestive heart failure in a subject. The assessment system includes a first interface configured to communicate with a device that delivers a stimulation signal to a vagus nerve of the subject, a second interface configured to capture heart electrical activity of the subject in response to the stimulation signal, and a processor and a non-transitory computer readable memory. The memory stores instructions that, when executed by the processor, cause the assessment system to determine and display heart rate dynamics and display a digital ECG signal in real-time in response to the stimulation signal.

Another embodiment relates to a titration assessment system for vagus nerve stimulation therapy treatment in a subject. The assessment system includes an ECG cable assembly configured to acquire an ECG signal response in the subject, a VNS titration assembly configured to deliver a periodic stimulation signal having ON-periods and OFF-periods, and a data acquisition system coupled to the ECG cable assembly and configured to capture the ECG signal response and detect delivery of the stimulation signal. The assessment system also includes a processor and a non-transitory computer readable memory storing instructions that, when executed by the processor, cause the assessment system to process the ECG signal to determine R-R intervals in the ECG signal corresponding to the ON-periods and the OFF-periods and digitally reproduce the ECG signal for display.

Another embodiment relates to a method of assessing a vagus nerve stimulation treatment for a subject. The method includes determining heart rate dynamics in an ECG signal response to the vagus nerve stimulation for a plurality of cycles of stimulation signal delivery. Each cycle is defined by an ON-period and an OFF-period of the stimulation signal. The method further includes digitally displaying the ECG signal in real-time and providing an indication of autonomic engagement of the subject within 20 cycles.

BRIEF DESCRIPTION OF THE DRAWINGS

The accompanying drawings, which are incorporated herein and constitute part of this specification, illustrate exemplary embodiments of the systems and methods described herein, and together, with the general description given above and the detailed description given below, serve to explain the features of the systems and methods described herein.

FIGS. 2A-2D are detailed views of graphical displays of FIG. 2, according to exemplary embodiments.

DETAILED DESCRIPTION

When delivering neurostimulation therapies to patients, it is generally desirable to avoid stimulation intensities that result in either excessive tachycardia or excessive bradycardia side effects. The neurostimulator may be adjusted to deliver varying stimulation intensities to the patient. To find a beneficial therapeutic level of neurostimulation, researchers have utilized the patient's heart rate changes. Some researchers have proposed that heart rate reduction serves as a functional response indicator or surrogate for effective recruitment of nerve fibers and engagement of the autonomic nervous system elements. Thus, autonomic engagement as a physiological response to vagus nerve stimulation may be indicative of a therapeutic level of neurostimulation. Accordingly, there remains a patient or clinician need for systems and methods that can capture and assess the physiological response to delivery of a vagus nerve stimulation signal.

Figure 1:
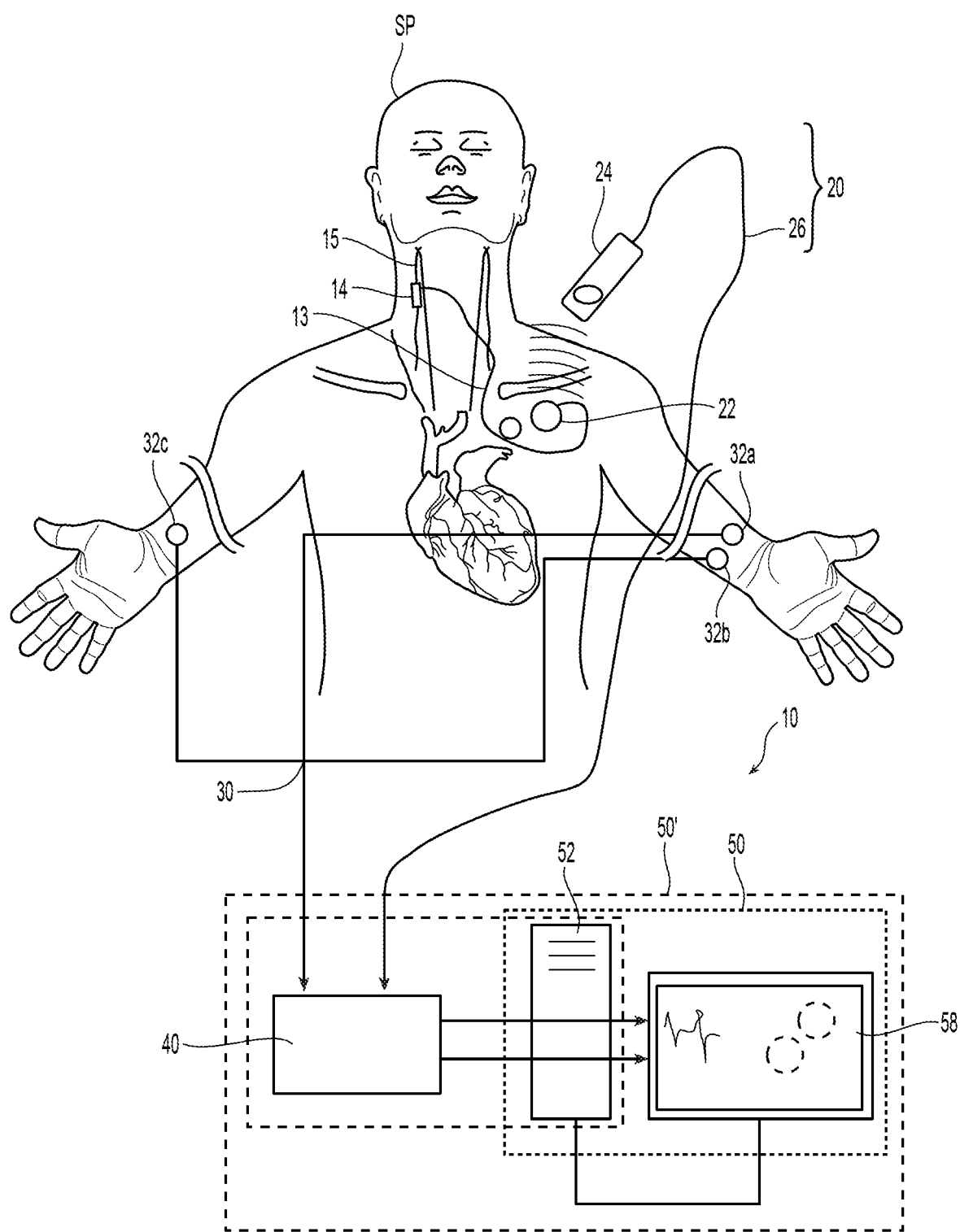
FIG. 1 a schematic view of a system for assessing vagus nerve stimulation for treatment of congestive heart failure, according to an exemplary embodiment.

Shown in FIG. 1 is a system 10 for monitoring and assessing a physiological response of a subject patient SP to neurostimulation therapy, and, in particular, a heart rate dynamic response to vagus nerve stimulation for the treatment of chronic heart failure ("CHF"). In various embodiments, the system 10 provides a patient and/or clinician with a display of the electrical heart activity, e.g., an electrocardiogram ("ECG") signal and heart rate dynamic response of the patient to the vagus nerve stimulation treatment. In addition, the accompanying ECG signal display provides a monitor for detecting or diagnosing any heart arrhythmias during the course of the vagus nerve stimulation therapy.

The system 10 captures the physiological response to the vagus nerve stimulation. In some embodiments, the system (i) detects the electrical heart activity response, e.g., ECG of the subject patient SP in response to the vagus nerve stimulation; (ii) determines the change in heart rate dynamics in response to the stimulation; and (iii) visually displays the change in heart rate dynamics along with a dynamic display of the ECG waveform response. The display is provided in a timeframe that is, for example, in real-time, which includes a timeframe that is instantaneous, immediate, sequential, or proximate to a parameter change; encompassing a titration session; and/or within one minute, ten minutes, and/or an hour of a stimulation parameter change. In some embodiments, the real-time display can allow and/or facilitate the modification of the stimulation therapy, the subject patient SP's advancement through the titration process, and/or the delivery of effective levels of therapy to the subject patient SP in a timeframe that is real-time, which includes a timeframe that is instantaneous, immediate, sequential, or proximate to a parameter change; encompassing a titration session; and/or within one minute, ten minutes, and/or an hour of a stimulation parameter change. By providing a visual feedback of physiological response and changes in heart rate dynamics (e.g., in real-time), the effectiveness of the stimulus treatment can be quickly assessed by the patient or clinician, and the stimulus can be adjusted as needed to ensure delivery of an effective stimulus or the delivery of a stimulus that advances the titration of the subject patient to an effective stimulus. Moreover, by assessing a stimulation signal of a titration process in real-time, the stimulation signal can be optimized, and the overall titration process and the therapy can be made more efficient by minimizing the time required to achieve a titrated delivery of a full therapeutic dose or intensity of a vagus nerve stimulus. Alternatively or additionally, the titration process can be automatically altered or increased in intensity with the detection, monitoring, and/or measurement by the system 10 occurring in real-time. The assessment can be read from system 10 in real-time, or, if needed or desired, the assessment can be read from the system 10 by a clinician at a later time in a clinic or other environment.

The system 10 includes a first interface or communication assembly 20 for communication with a stimulation delivery device 22 and a second interface assembly 30 for capturing the physiological response of the subject patient SP. In some embodiments, the second interface assembly 30 captures data suitable for generating the ECG waveform response of the subject patient SP to the stimulation delivery. In various embodiments, as shown in FIG. 1, the stimulation delivery device 22 is embodied as an implantable medical device ("IMD") and, more particularly, an implantable neurostimulator 22. Embodiments of the neurostimulator 22 are shown and described in U.S. Pat. Nos. 9,770,599 and 9,950,169, each of which is incorporated by reference in its entirety. As described in the cited patent documents, the implantable medical device includes a pulse generator 22, a lead 13, and electrodes 14 for delivering a pulse generated stimulus about a vagus nerve 15 of the subject patient SP. A commercially available embodiment of the implantable neurostimulator 22 includes the VITARIA™ Model 7103 Pulse Generator from LivaNova USA, Inc. of Houston, Tex., USA.

Figure 1A:
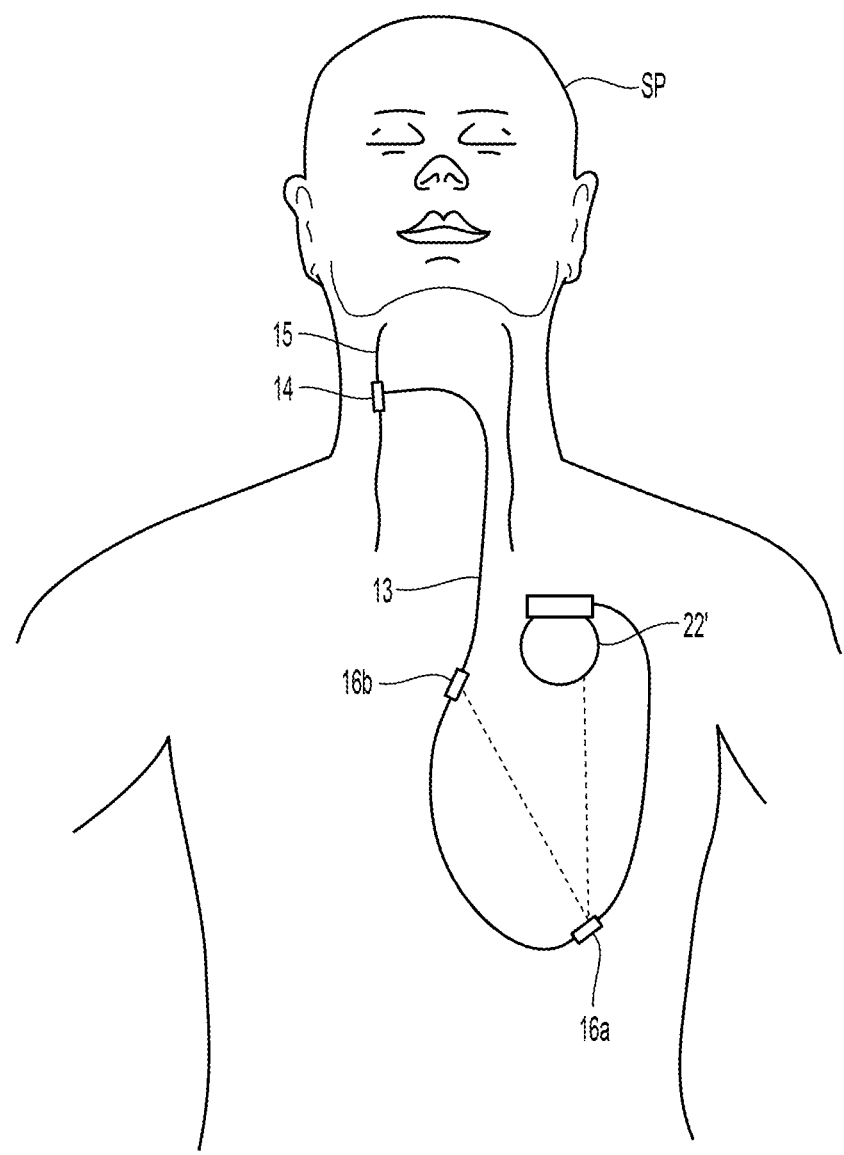
FIG. 1A is another schematic view of a neurostimulator for use in the system of FIG. 1, according to an exemplary embodiment.

Shown in FIG. 1A is another embodiment of a neurostimulator 22', for use with the assessment system 10, which includes or incorporates an implantable cardioverter-defibrillator ("ICD"). An implantable VNS/ICD system is also shown and described in U.S. Pat. No. 9,770,599, which is incorporated by reference in its entirety. An embodiment of an implantable VNS/ICD system includes a pulse generation module with a control system, a VNS subsystem, and an ICD subsystem. A first electrode assembly 14 is coupled to the pulse generation module and includes a VNS electrode configured to couple to the vagus nerve 15. A second electrode assembly 16a, 16b is coupled to the pulse generation module and includes a subcutaneous electrode. Another embodiment of an implantable VNS/ICD system includes a primary pulse generation module having a primary control system and an ICD subsystem and a secondary pulse generation module having a secondary control system and a VNS subsystem. The secondary pulse generation module is placed in data communication with the primary pulse generation module, with the second electrode assembly 16a, 16b coupled to the primary pulse generation module, in which the second electrode assembly 16a, 16b includes a subcutaneous electrode. Another electrode assembly is coupled to the secondary pulse generation module. This electrode assembly includes a VNS electrode 14 configured to couple to the vagus nerve 15. In various embodiments, the implantable VNS/ICD system is configured to deliver a chronic VNS therapy to the vagus nerve 15 with a VNS subsystem of a pulse generation module. In response to detection of a cardiac event, the implantable VNS/ICD system is configured to deliver electrical cardioversion-defibrillation energy with an ICD subsystem of the pulse generation module.

Figure 6:
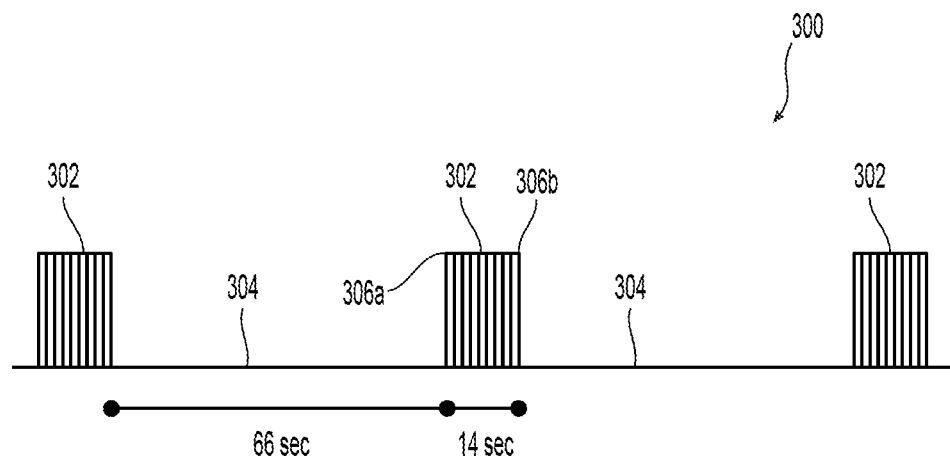
FIG. 6 is an illustrative schematic view of a stimulus signal, according to an exemplary embodiment.

An illustrative stimulation signal 300 is shown in FIG. 6. The stimulation signal 300 is periodically delivered in a cyclical manner in which each cycle has an ON-period 302 in which a stimulation signal of a particular current amplitude and frequency is delivered to the vagus nerve and an OFF-period 304 of rest in which no stimulation signal is delivered. The ON-period 302 occurs at a constant interval with the OFF-periods 304 of rest between the repeating ON-periods 302. In some embodiments, a treatment cycle can be defined by a combination of on and off times selected from the following exemplary ON-periods: 7 sec, 14 sec, 21 sec, 30 sec, 50 sec, and 60 sec; and exemplary OFF-periods:

12 sec, 18 sec, 24 sec, 30 sec, 42 sec, 54 sec, 66 sec, 78 sec, 90 sec, 120 sec, 180 sec, and 300 sec. For example, one exemplary treatment cycle is defined by a 14 second "on period" and a 66 second "off period." A cycle of stimulation delivery is defined by a continuous series of ON-periods 302 and OFF-periods 304. In one treatment, there are fewer than twenty cycles (e.g., ranging between 5-10 cycles) delivered to the subject patient.

Figure 6A:
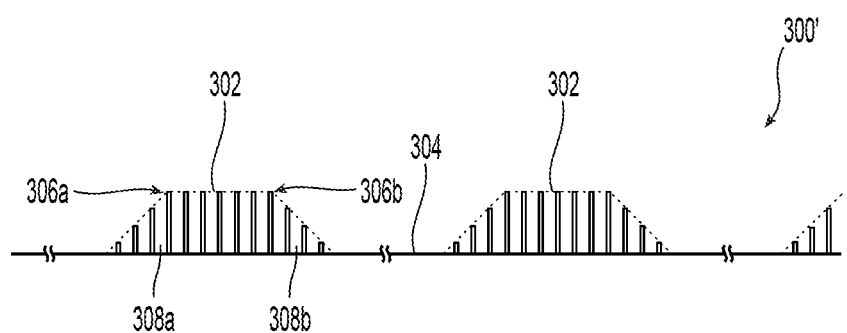
FIG. 6A is an illustrative schematic view of another stimulus signal, according to an exemplary embodiment.

Each UN-period 302 is defined by repeating pulse signals at a defined output current amplitude or intensity, signal frequency, and pulse width. In one exemplary ON-period 302, the pulse signals are defined by an output current of up to 3.0 mA, a frequency of 5-10 Hz, and a pulse width at 250-300 micro-seconds ("pee"). Accordingly, each ON-period 302 is defined by an initiating pulse 306a and a terminating pulse 306b that are spaced apart over a time duration defining the ON-period 302. The OFF-period 304 is thus defined by the time duration between a terminating pulse 306b of one ON-period 302 and the initiating pulse 306a of the subsequent ON-period 302. Shown in FIG. 6A is another embodiment of a stimulation signal 300', which includes a ramp up period 308a to the initiating pulse 306a and a ramp down period 308b from the terminating pulse 306b.

Figure 7:
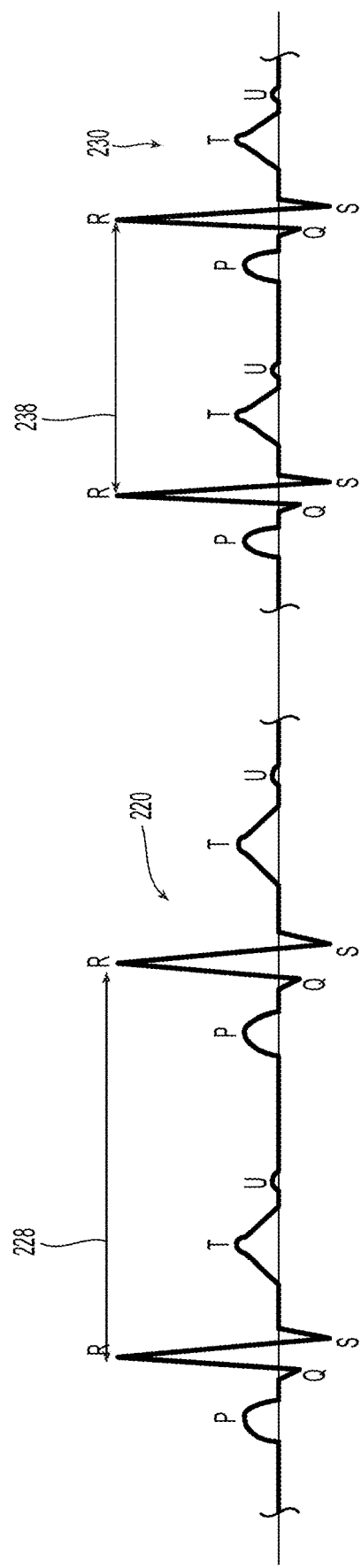
FIG. 7 is an illustrative view of an ECG waveform response of a subject patient to a vagus nerve stimulation treatment.

FIG. 7 is an illustrative ECG waveform response over ON- and OFF-periods. An ECG-suitable signal is a periodic waveform with repeating "cardiac cycles." A "cardiac cycle" may refer to one complete PQRSTU interval of the patient's heart functioning, ending with the P wave of the next succeeding cardiac cycle. An "interbeat interval" may refer to the time period between a predetermined point in a first cardiac cycle of the patient and the same predetermined point in the immediately succeeding cardiac cycle of the patient. Examples of interbeat intervals include an R-R interval, a P-P interval, or a T-T interval. Interbeat intervals may include a single interval or a moving average (either simple or weighted) of several consecutive intervals. Within a single cardiac cycle, a "cardiac period" is a length of time between a first point in the cardiac cycle of the patient and a second, later point. An exemplary cardiac period includes a P-wave, a Q-wave, an R-wave, an S-wave, a QRS complex, a T-wave, and a U-wave of the cardiac cycle, which can be readily identified by electrocardiography or other techniques of monitoring the electrical activity of the heart. For example, the R-wave presents the maximum amplitude of the cardiac cycle.

Referring back to FIG. 1, in the system 10, a computer processing device 50 is coupled with the first and second interfaces 20, 30 for ECG-suitable signal processing and generating a graphic output display in a manner as described herein. In some embodiments, the output is generated in real-time, synchronized with the delivered stimulation signal so that the effects of the stimulation delivery can be rapidly assessed. In some embodiments, the computer processing device 50 can be embodied using a general purpose programmable computer. A general purpose programmable computer can be a personal computer, laptop computer, Ultrabook computer, netbook computer, handheld computer, tablet computer, smart phone, or other form of computational device with an appropriate operating system. In other embodiments, the computer processing device 50 can be a specialized computer specifically designed and programmed to function with the neurostimulator 22 described herein.

Figure 2:
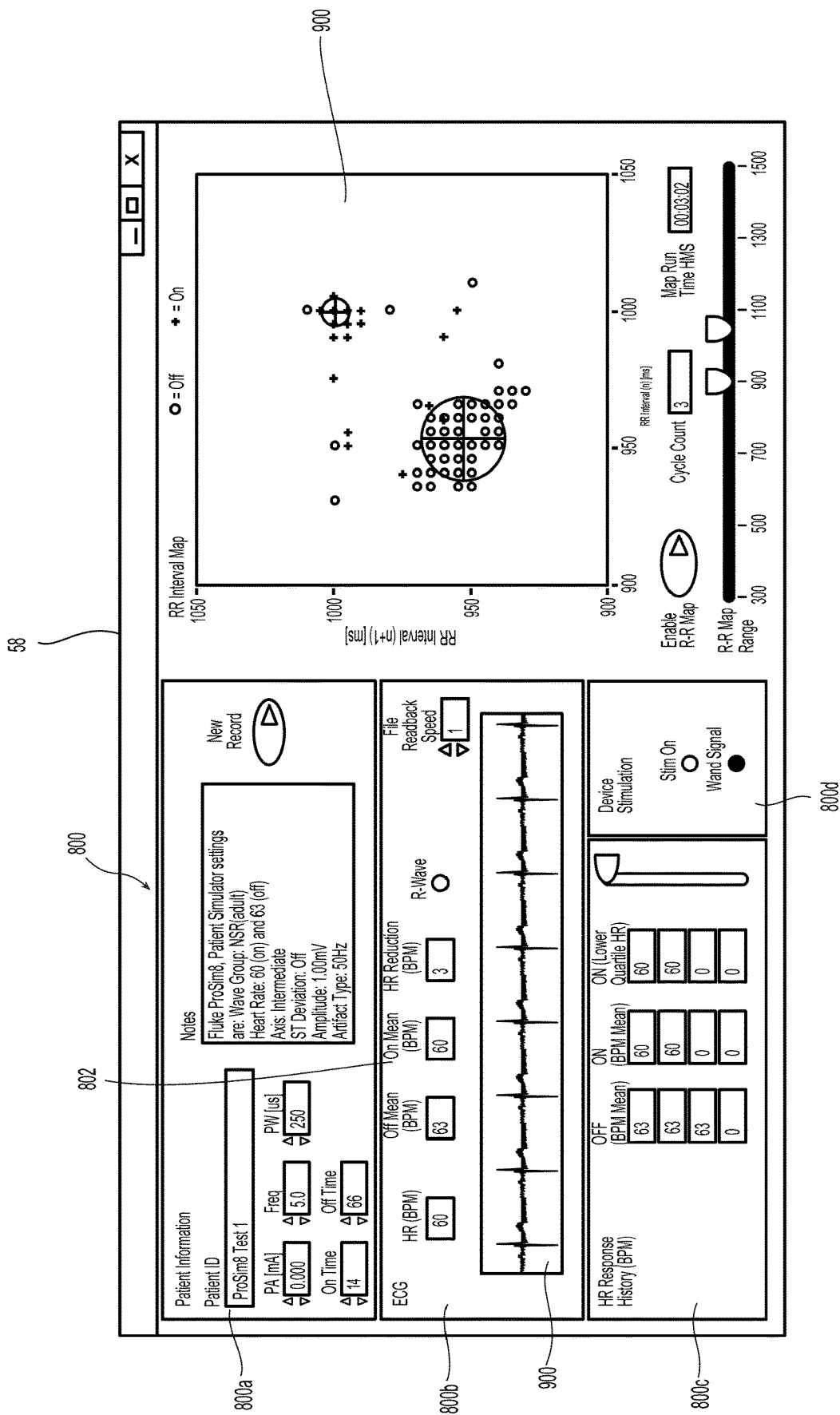
FIG. 2 is a graphic display for use in the system of FIG. 1, according to an exemplary embodiment.

The computer processing device 50 includes one or more associated displays 58 for displaying the subject patient SP's ECG and/or heart rate dynamic response to the vagus nerve stimulation (e.g., to the subject patient SP or assisting clinician). The display 58 can be a touch-sensitive display that can provide touch control buttons and keys. Shown in FIG. 2 is an embodiment of a computer-generated output to display 58. In some embodiments, the computer-generated output shown in FIG. 2 is generated in a Windows® environment or similar operating system. The computer-generated output includes a graphical user interface ("GUI") 800 having one or more graphical user interface elements 802 and a dynamic, digitized, replicated ECG waveform display 900. The computer processing device 50 and its hardware includes and executes firmware programming that carries out the assessment methods and generation of output displays described herein. The methods and displays can be implemented using appropriate software programming for signal processing and hardware configuration. For example, an appropriate "graphical program" can be used to represent data structures and/or program instructions in memory (e.g., system memory 56a and/or storage memory 56b of FIG. 3) of the computer processing device 50 to carry out the signal processing, instrument access, assessment methods, GUI output, and display generation described herein. An exemplary graphical program development environment in which to create a program for use in the system 10 includes LabVIEW from National Instruments Corp.

FIGS. 2A-2D show detailed views of displays 800a-800d and ECG waveform display 900 from the GUI 800 of FIG. 2, according to exemplary embodiments. As shown in FIGS. 2A-2D, the displays 800a-800d and 900 provide various heart rate dynamic calculations of the subject patient and information about the delivered stimulation signal. Heart rate dynamic responses are determined under a condition in which a stimulation signal is delivered to the vagus nerve and under a resting condition in which no stimulation is delivered to the vagus nerve. In some embodiments, the heart rate dynamics are determined as a function of R-R interval time between adjacent R-waves of the ECG waveform response to the stimulation signal over time. An autonomic engagement response can be determined by showing a sufficient change in the heart rate during the delivered stimulation period as compared to the resting period. Thus, the system 10 can provide a visual assessment of the delivered stimulation signal.

More specifically, in FIGS. 2A-2D, various elements of the GUI 800, such as, for example, visual indicators, can be provided to indicate the heart rate response of the subject patient. In FIG. 2A, the display 800a shows the following heart rate dynamic value indicators (in beats per minute ("BPM")): real-time heart rate (804a), the mean heart rate for each of the OFF-periods (804b), the mean heart rate for each of the ON-periods (804c), and the heart rate reduction (804d). The displayed values 804a-804d can provide the user and/or the clinician an assessment of the delivered stimulus in a manner as is described herein along with definitions of each of the heart rate dynamic parameters.

In some embodiments, the computer processing device 50 determines and displays the heart rate dynamics results in real-time. Alternatively, the results can be displayed after a number of cycles of stimulation signal delivery. For example, the results can be returned within 20 cycles or less of stimulation delivery (e.g., within 10 cycles, within 5 cycles).

The GUI 800a also includes a digital reproduction of the ECG-waveform response signal 900 to show, for example, a real-time physiological response to the stimulation signal. Moreover, the digital response 900 can serve as an additional diagnostic tool by providing a visual indicator of any possible heart arrhythmias. In some embodiments, the digital display 800*a* is dynamic, playing or scrolling across the screen in real-time with updates to the heart rate dynamic values 804*a*-804*d*. Additionally, in some embodiments, the GUI 800*a* includes a readback speed control 902 to control the playback speed of the ECG signal response.

Figure 2E:
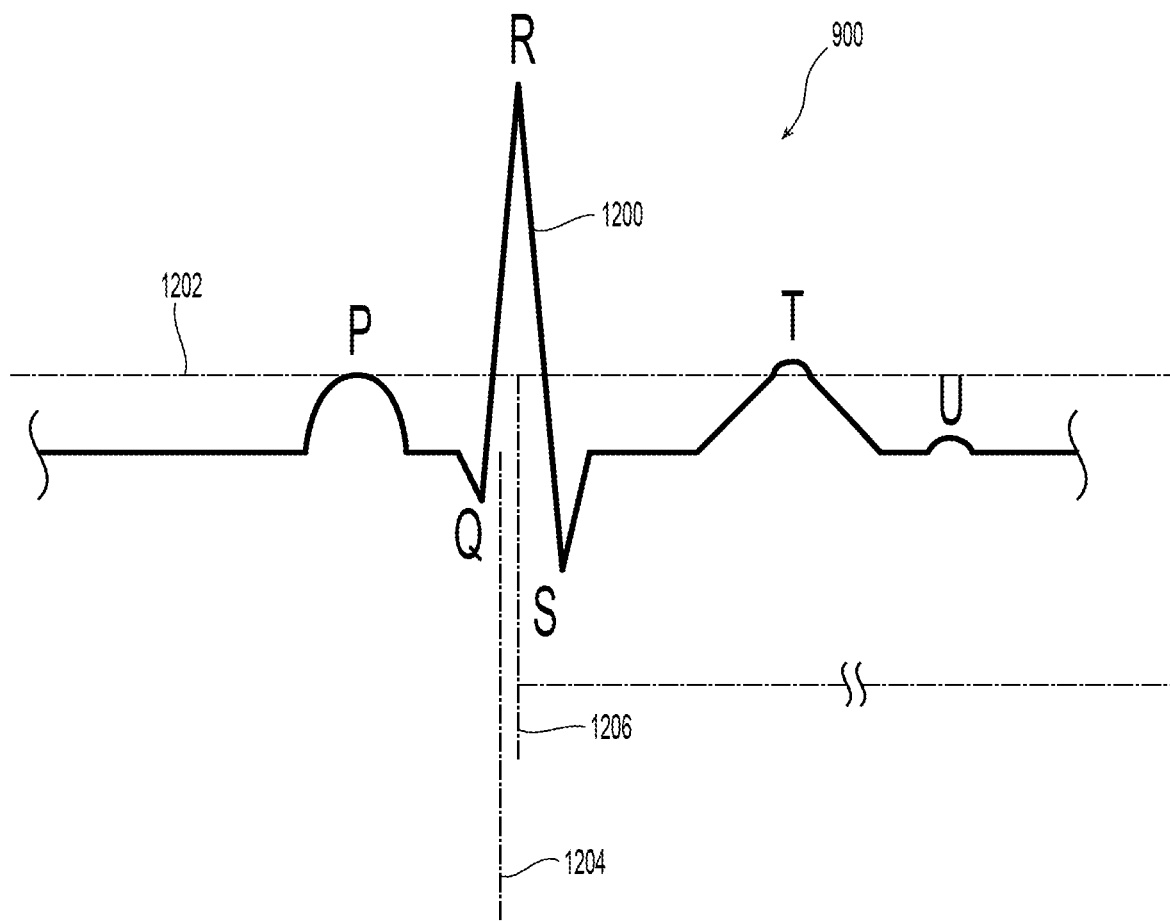
FIG. 2E is an illustrative ECG waveform detail of the graphical display in FIG. 2B, according to an exemplary embodiment.

Shown in FIG. 2E is a detailed view of a PQRSTU interval 1200 in the digitally generated ECG waveform response 900. The digital ECG waveform display 900 provides a quality check on the digitally replicated signal. For example, the display 900 includes a baseline indicator or axis 1202, a beat indicator axis 1204, and an R-wave axis indicator 1206. In one aspect, the R-wave axis 1206 can provide for a quality check of the digital reproduction by its spacing from the beat indicator axis 1204. For example, greater alignment between the R-wave axis 1206 and the beat axis 1204 can indicate the quality of the reproduction. Each of the waveform intervals 1200 and the indicators 1202, 1204, 1206 can be visually distinguishable from one another. For example, the axes 1202, 1204, 1206 may be defined by varying line thickness or dash treatment. In some embodiments, the displayed lines are distinguished by color. For example, the intervals 1200 of the ECG signal can appear in green, the baseline indicator 1202 in yellow, the beat indicator 1204 in red, and the R-wave indicator 1206 in white for contrast against a black background.

Referring back to FIG. 2B, the GUI 800 shown on the display 58 can include a window 800*b* of displayed information regarding patient information and the stimulation signal itself. The information can be acquired from the communication interface 20 or, alternatively, entered into the computer processing device 50 directly. The displayed information can include a patient ID 806 and at least one of the following stimulation signal parameters: current amplitude 808*a* (e.g., measured in milliamps (mA)), current frequency 808*b* (e.g., measured in Hz), pulse width 808*c* (e.g., in micro seconds), duty cycle ON-period time 808*d* (e.g., measured in seconds), and duty cycle OFF-period time 808*e* (e.g., measure in seconds). Additional GUI elements can be provided, for example, a new record creation button 810*a* and/or a notes summary window 810*b*. FIGS. 2C and 2D are discussed in further detail below.

Figure 3:
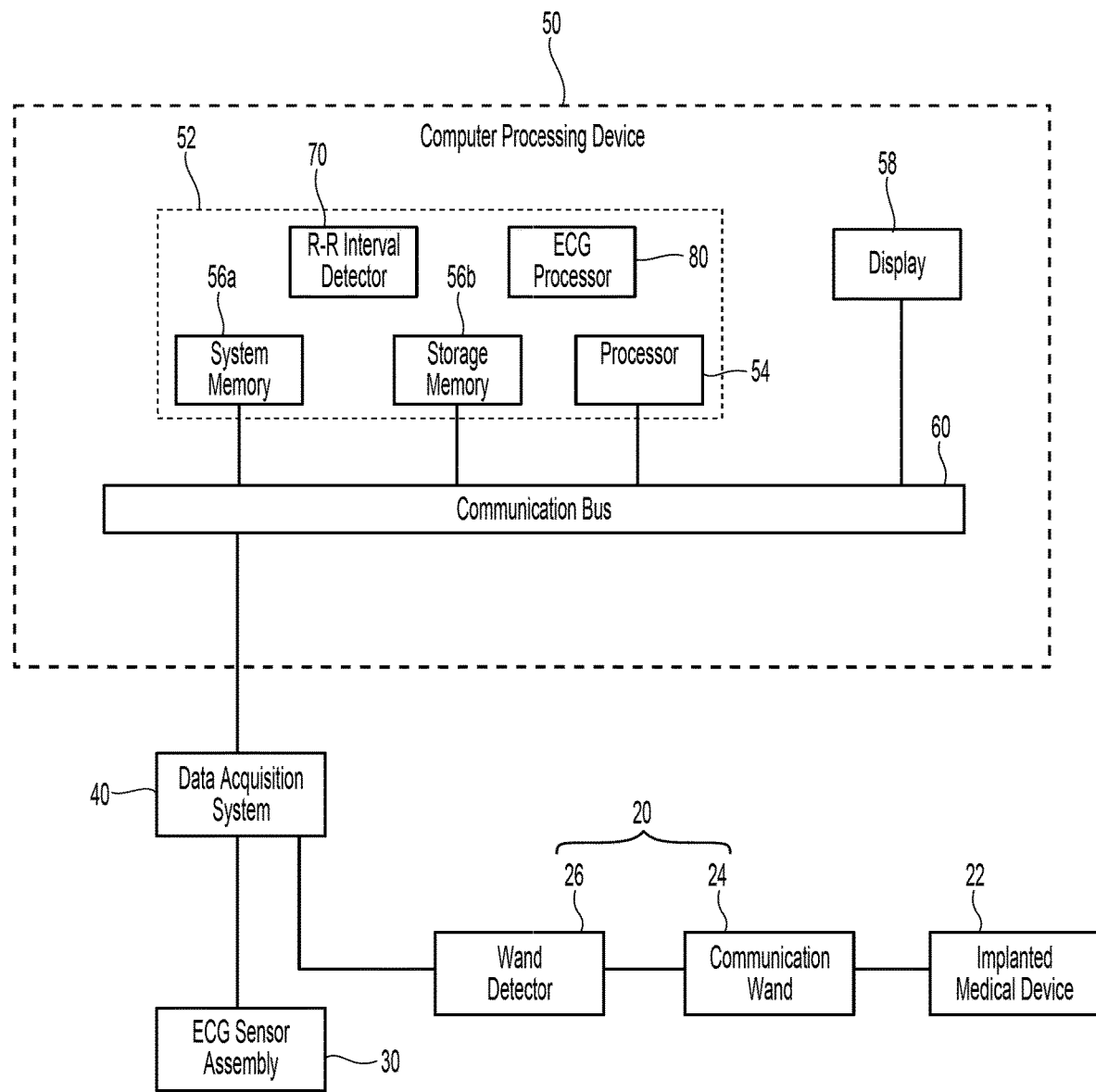
FIG. 3 is a schematic view of components of the system of FIG. 1, according to an exemplary embodiment.

Shown in FIG. 3 is another schematic view of the system 10 with the computer processing device 50 for assessing a vagus nerve stimulation treatment, according to an exemplary embodiment. The computer processing device 50 includes processing hardware 52, such as, for example, a central processing unit 54 and associated memory or computer readable medium, such as, for example, system memory 56*a* and storage memory 56*b*, for storing and processing ECG-suitable signals in a manner as described herein. The system memory 56*a* can include volatile memory, such as, for example, RAM (random-access memory). The storage memory 56*b* can be non-volatile or persistent memory such as, for example, ROM (read-only memory), flash memory, ferroelectric RAM, most types of magnetic computer storage devices (e.g. hard disk drives, solid state drives, floppy disks, and magnetic tape), or optical discs.

The computer processing device 50 operates under the control of one or more software applications, which are executed as program code as a series of process or method modules or steps by the programmed computer hardware. In some embodiments, a computer readable medium, such as a non-transitory computer readable medium, of the processing hardware SL stores a program that can cause the computer processing device 50 to execute one or more processes described herein for assessing vagus nerve stimulation treatment. Accordingly, in some embodiments, the system memory 56*a* and/or storage memory 56*b* may store instructions that are executable by the processor 54 to perform the functionalities described herein. The hardware 52 includes and executes firmware programming that provides for an R-R interval detector 70 and an ECG processor 80 for carrying out the assessment methods and displaying the assessment as described herein. The R-R interval detector 70 and the ECG processor 80 and the associated methods can be implemented using appropriate software programming, such as, for example, an appropriate graphical program as previously described.

As shown, the processing hardware 52 and the display 58 communicate with one another over a communication bus or network 60. Additionally or alternatively, the computer processing device 50 can include one or more peripheral input and output ports for connection and use with other peripheral input, output, or storage devices. The components of the computer processing device 50 can be integrated with one another or be separately housed components. For example, the processing hardware 52 can be housed separately from the display 58. Alternatively, the display 58 can be housed with the processing hardware 52 in a single assembly.

Referring back to FIG. 1, in the system 10, the computer processing device 50 is coupled to each of the first and second interface communication assemblies 20, 30 by a data acquisition system 40. The data acquisition system 40 provides for digital conversion of incoming signals coming from the interface communication assemblies 20, 30 (e.g., a wand assembly 20, ECG sensor assembly 30). The data acquisition system 40, the processing hardware 52, and the display 58 communicate with one another over the communication bus or network 60 (e.g., as shown in FIG. 3). In some embodiments, the data acquisition system 40 for use in the system 10 is the BIOPAC MP36R from BIOPAC® Systems, Inc., which can simultaneously capture signals from multiple devices or sources. Additionally, in some embodiments, the computer processing device and data acquisition system are different systems (e.g., shown as computer processing device 50 and data acquisition system 40 in FIG. 1), while in other embodiments, the computer processing device and data acquisition system are incorporated into a single system (e.g., shown as computer processing device 50' in FIG. 1).

In the system 10, the communication assembly 20 wirelessly communicates with the neurostimulator 22 by providing control signals or commands to define parameters of the stimulation signal or pulses to be delivered by the neurostimulator 22 to the vagus nerve 15. In some embodiments, as shown in FIG. 1, the communication assembly 20 includes an external programming wand 24 and a wand transmission detection cable 26. The programming wand 24 wirelessly communicates with the implanted device 22 by telemetry or radio frequency ("RF") signal. Embodiments of the external programming wand 24 are described, for example, in U.S. Pat. Nos. 9,770,599 and 9,950,169. A commercially available embodiment of the wand 24 includes NeuroCybernetic Prosthesis (NCP®) Programming Wand Model 201. The wand 24 is a hand-held device that can transmit programming and interrogation information signals or commands to the implantable neurostimulator 22, such as, for example, the VITARIA™ Model 7103 Pulse Generator. The programming wand 24 alone or in conjunction with a computer and appropriate firmware, such as, for example, VNS Therapy Programming Software, can store and retrieve telemetry data and revise stimulus signal parameters from the pulse generator 22.

The wand transmission detection cable 26 is associated with the external programmer or wand 24 to detect or determine the stimulation delivery from the neurostimulator 22 to the vagus nerve 15 of the subject patient SP. In some embodiments, the detection cable 26 detects or extracts the delivery schedule from the external wand 24 to determine the stimulation delivery from the neurostimulator 22 to the vagus nerve 15. By detecting delivery of stimulation signals with the communication assembly 20, the capture or recording of the subject's ECG-suitable signal can be synchronized with the ON-period and OFF-period of the stimulation signal in accordance with the processes for capturing and analyzing the ECG-suitable signal described herein.

In some implementations, the second interface assembly 30 is embodied as an ECG cable assembly with three leads or clips 32a, 32b, 32c for respectively connecting to three electrodes or contacts, for example, placed on the wrists of the subject patient SP. As seen in FIG. 1, two leads 32a, 32b are connected to two electrodes on the left wrist, and the remaining lead 32c is connected to a single electrode on the patient's right wrist.

Figure 4:
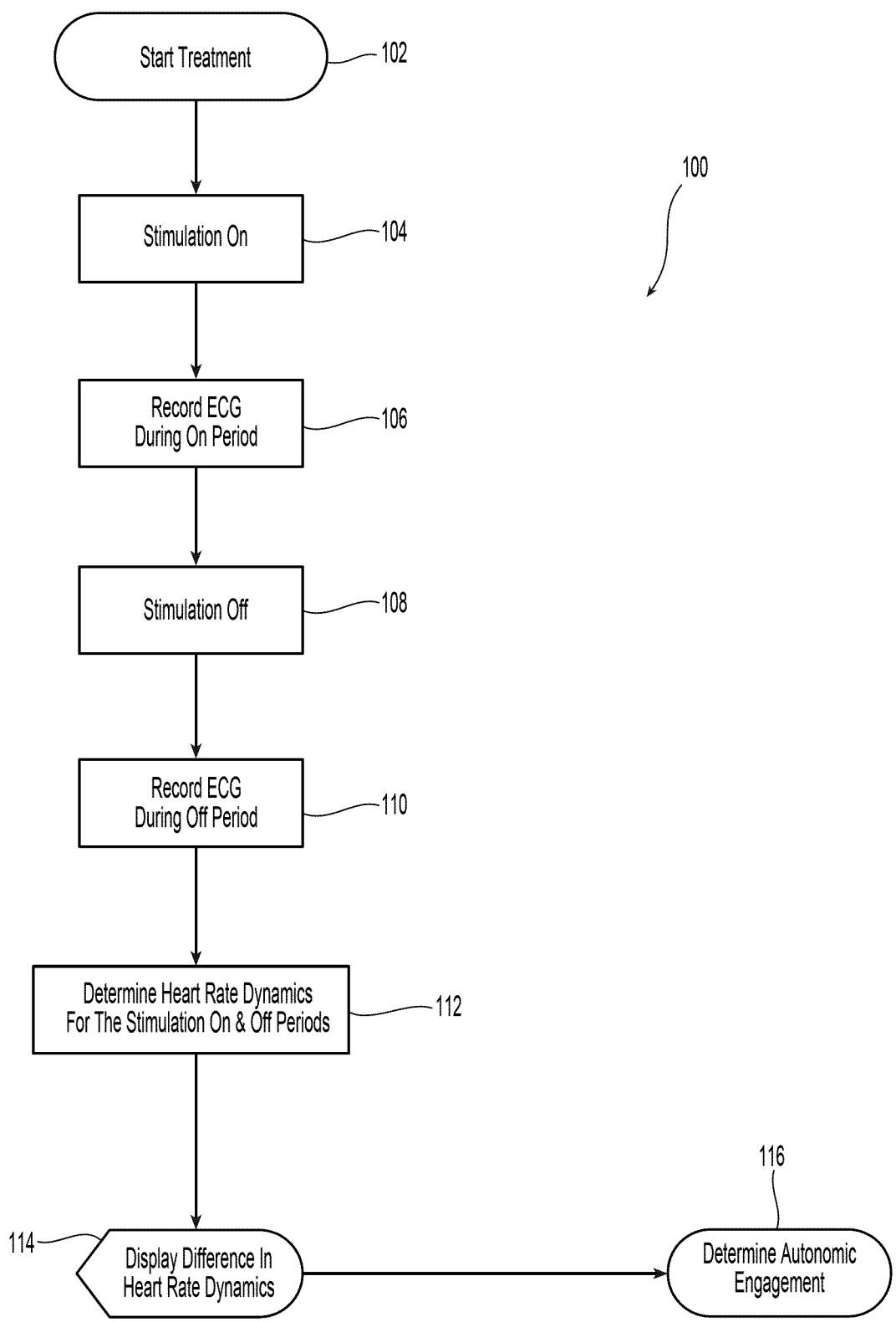
FIG. 4 is an embodiment of a method for assessing autonomic engagement response to vagus nerve stimulation therapy using the system of FIG. 1.

Shown in FIG. 4 is a method of using the system 10 in which determination and display of the heart rate dynamic response provides an indication or assessment of autonomic response to vagus nerve stimulation in congestive heart failure treatment of a subject patient. In one embodiment of the system 10 and its operation 100, the system 10 processes the ECG signal response to determine the ECG waveform and the R-R intervals of the ECG signal response to derive heart rate dynamics in assessment of the stimulus treatment. Moreover, the system 10 distinguishes or identifies which portions of the ECG signal or waveform response correspond to the delivery of a stimulation signal (e.g., over the ON-period of the periodic stimulation signal) and which portions of the ECG signal or waveform response correspond to the rest period of the stimulation signal (e.g., over the OFF-periods of the periodic stimulation signal). By segregating ECG signals or portions of the ECG waveform and their derivative components by ON-period and OFF-period, the ECG signals/waveforms and the heart rate dynamics derived therefrom are compared between the ON-period and the OFF-period to assess the extent of autonomic engagement resulting from the delivered stimulation signal.

At a beginning 102 of a titration or stimulation delivery process, the periodic stimulation signal is delivered from the neurostimulator 22 to the vagus nerve. During the ON-period of the stimulus delivery (step 104), a recordation step 106 is carried out in which the ECG response signal is captured and recorded over the ON-period. During the OFF-period of the stimulation signal (step 108), the ECG response signal is captured and recorded at step 110. Having captured and identified the ECG signals corresponding to each of the ON-period and OFF-period in the stimulation signal, a determination step 112 is carried out to determine the heart rate dynamics and, in particular, heart rate variability for the ON- and OFF-periods. The difference or differential in heart rate dynamics between the ON- and OFF-periods of the stimulation signal is determined and displayed in step 114. The process then concludes with a determination step 116 in which the autonomic engagement response is assessed and determined from the differential between the heart rate dynamics for the ON- and OFF-periods.

Referring again to FIG. 3, the ECG processor 80 includes a heart rate variability calculator that works with the R-R interval detector 70 to determine heart rate dynamics in the determination step 112 of the assessment process 100. In an aspect, the storage memory 56b, in coordination with the R-R interval detector 70 and ECG processor 80, stores in one or more data arrays the R-R interval for each proceeding R-R interval and stimulation status ON/OFF period for number of cycles in the stimulation treatment. Accordingly, the stored data array can be darned as {R-R Interval(N+1), R-R Interval(N), ON/OFF-period Status, #Cycle}.

Figure 5:
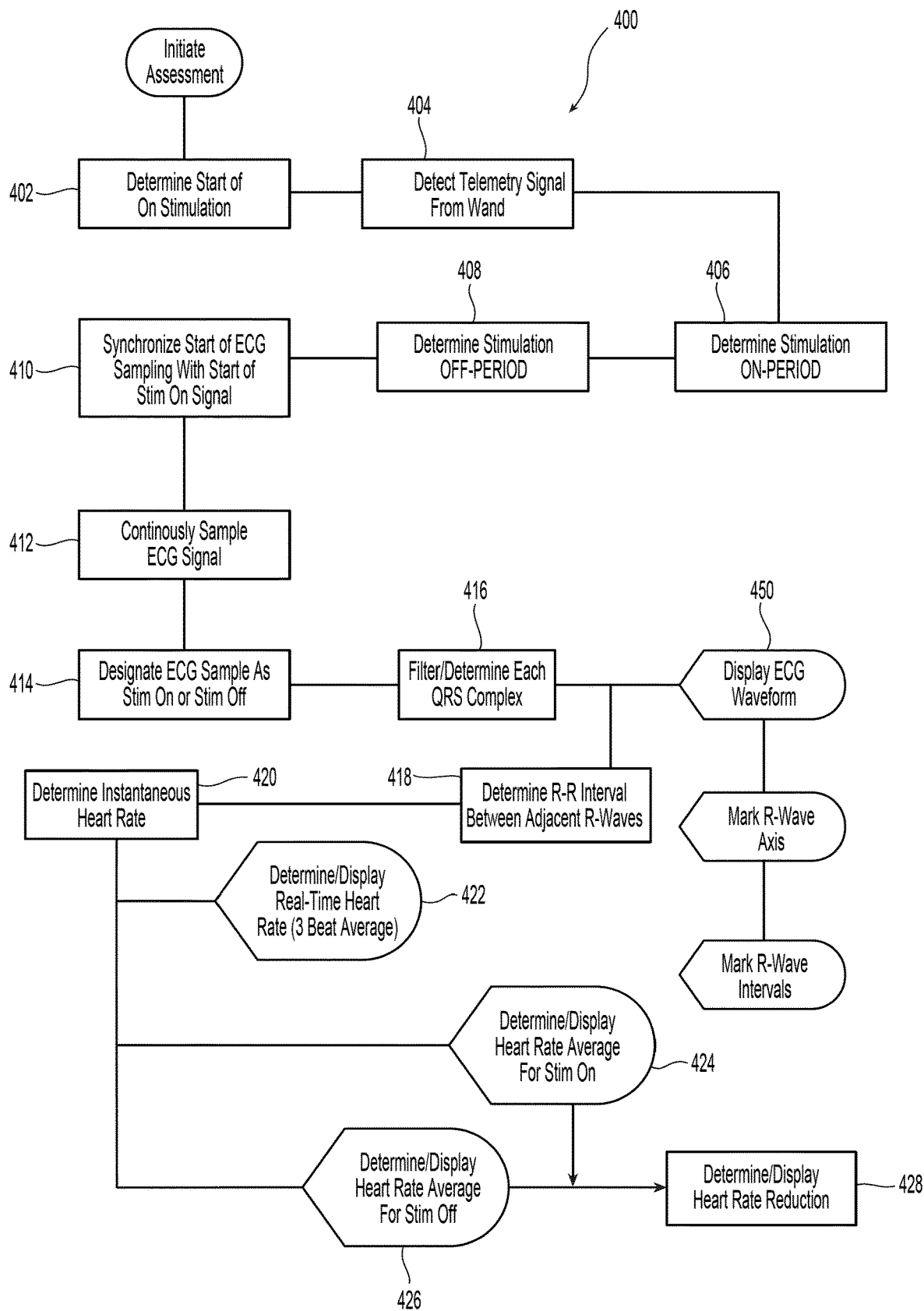
FIG. 5 is another embodiment of a method for assessing autonomic engagement response to vagus nerve stimulation therapy using the system of FIG. 1.

Shown in FIG. 5 is an embodiment of the assessment process 400. With the subject patient SP connected to the system 10, as shown in FIG. 1, and the implanted neurostimulation medical device 22 delivering a stimulation signal to the vagus nerve of the patient, the process of assessment 400 begins with a determination step 402 to determine the start of stimulation delivery for synchronizing recordation of the cardiac response. In some embodiments, the programming wand 24 is placed in communication with the neurostimulator 22, and the wand transmission detection cable 26 in combination with the computer processing device 50 detects the inductive telemetry signal between the components (step 404). The computer processing device 50 processes the inductive telemetry signals to determine the stimulation ON-period (step 406) and determine the stimulation OFF-period (step 408). In an aspect, an output window 800c as shown in FIG. 2C can be provided via the display 58 to indicate transmission from the wand 24 and/or stimulation delivery by the neurostimulator 22. Additionally, in some embodiments, the computer processing device 50 captures the various defining parameters of the delivered stimulation signal from which recordation of the ECG or cardiac response can be synchronized. At step 410, the computer processing device 50 synchronizes sampling of the ECG-suitable signal with the start of the ON-period of the delivered stimulation signal (e.g., such that the ECG-suitable signal is continuously recorded). With the start of ECG recording synchronized with the stimulation signal, the ECG response signal is continuously sampled at step 412 by the data acquisition system 40 and the computer processing device 50. For example, the ECG-suitable signal is sampled at a rate of 200 samples per second at a rate suitable for analysis and processing as described herein. In some embodiments, the ECG-suitable signal is recorded for at least one successive pair of ON- and OFF-periods. More particularly, in some embodiments, the ECG-suitable signal is recorded over a plurality of successive pairs of ON- and OFF-periods.

In an exemplary ECG processing step 414, the digitally converted ECG-suitable signal is segregated and designated into portions that correspond to the ECG response to the ON-period of stimulation delivery and the ECG response to the resting OFF-period. Illustrated in FIG. 7 is a first portion 220 of the sampled ECG-suitable signal corresponding to the ON-period of the stimulation signal and a second portion 230 of the sampled ECG-suitable signal corresponding to the OFF-period of the stimulation signal. Each of the designated portions 220, 230 of the ECG response is then processed to determine its waveform components for analysis and digital reconstruction. Indicated in FIG. 7 are QRS complexes for the ON-period ECG waveform portion 220 and QRS complexes for the OFF-period ECG waveform portion 230. FIG. 7 also includes R-R intervals (228 for the first portion 220, 238 for the second portion 230), or time periods between adjacent R-waves in the ECG waveform or equivalent ECG characterization. Accordingly, in various embodiments, the R-R interval detector 70 of FIG. 3 determines and verifies the R-R intervals to complete the determination and filter steps 416, 418 in the process 400 of FIG. 4. With each R-wave and R-R interval identified within the ECG waveform or equivalent, the computer processing device 50 determines one or more heart rate dynamics for assessment of the delivered stimulation signal.

Referring again to FIG. 3, the ECG processor 80 is configured to calculate and provide one or more of the following: a heart rate, a heart rate variability, and digital ECG waveform. In some embodiments, in accordance with step 420 of the process 400 of FIG. 5, for each R-R interval, the instantaneous heart rate ("IHR") in beats per minute is determined by the following:

$$IHR = 1 \text{ beat}/(R\text{-}R \text{ interval msec}) \times (1000 \text{ msec/sec}) \times (60 \text{ sec/min})$$

From the IHR several statistical aspects of the heart rate can also be determined. In some embodiments, the real-time heart rate can be determined at step 422 by taking a beat-to-beat average over a range of the latest recorded number of beats. For example, the real-time heart rate ("RTHR") can be determined by the average of the last five or fewer instantaneous heart rates. Further, the RTHR can be output for display in the heart rate window 804a of the output display 800a in FIG. 2A. As can be appreciated, the IHR values can be qualified values that meet a threshold level of data quality, with inaccurate or inconsistent IHR values being disregarded, discounted, weighted, or modified to improve the quality of the IHR values used in the determination of the RTHR value. As can also be appreciated, the IHR(N) values, where N represents the most recent IHR values, can be ordered in time in a sequence with each value being adjacent to the next in time, ordered in time in a sequence with unqualified IHR values interposed between qualified IHR values and/or ordered in time in a sequence with a skipped IHR value or values interposed between qualified IHR values.

In a continuous manner, the storage memory 56b, in coordination with the R-R interval detector 70, stores in one or more data arrays each IHR, associated verified R-R interval, associated status identifier as either ON-period or OFF-period, and associated cycle number in the number of cycles defining the stimulus treatment. The ECG processor 80 determines, in real-time for display, the mean heart rate for each ON-period of stimulation signal delivery and OFF-period of rest in a given treatment cycle in steps 424, 426, respectively, of the process 400. For example, where a stimulation signal cycle is defined by a 14 second ON-period and a 66 second OFF-period, the ECG processor 80 takes the cumulative average of most or all the IHRs over the 14 second ON-period to determine the ON-period mean heart rate ("(MHR)ON") for display in the ON-period mean window 804c of the output display 800a in FIG. 2A. To determine the OFF-period mean heart rate ("(MHR)OFF"), the ECG processor 80 takes the cumulative average of most or all IHRs over the 66 second OFF-period for display in the OFF-period mean window 804b of output display 800a in FIG. 2A.

In step 428 of process 400 of FIG. 5, the ECG processor 80 determines (e.g., in real-time) the extent of bradycardia response. For example, the ECG processor 80 determines a heart rate reduction response for each cycle of treatment by determining the difference between the cumulative averages of the instantaneous heart rates to indicate a heart rate reduction ("HRR") as follows:

$$HRR = (MHR)OFF - (MHR)ON$$

A positive HRR indicates a bradycardia response, and a negative HRR indicates a tachycardia response. A positive HRR reduction of less than 5% from the mean heart rate for the OFF-period ((MHR)OFF) indicates a desired response of autonomic engagement. In various embodiments, the heart rate reduction HRR is displayed in the heart rate reduction window 804d of output display 800a in FIG. 2A.

Given the data compiled and collected by the computer processing device 50, the ECG processor 80, in step 450 of the method 400 of FIG. 5, generates and displays the digital replica of the ECG waveform 900 in the display 800a in real-time, as previously described and seen in FIG. 2A and detailed in FIG. 2E. Additionally, the history of heart rate dynamics can be displayed in an output display window 800d of FIG. 2D. The historical data can be historically arranged by stimulation cycle in the display 800d. Additionally, the historical data can be archived and can include one or more of the real-time heart rate (RTHR), the mean heart rates for each of the OFF-period and ON-period ((MHR)OFF, (MHR)ON), and the heart rate reduction (HRR).

For the purpose of this disclosure, the term "coupled" means the joining of two members directly or indirectly to one another. Such joining may be achieved with the two members or the two members and any additional intermediate members being integrally formed as a single unitary body with one another, or with the two members or the two members and any additional intermediate members being attached to one another. Such joining may be permanent in nature or may be removable or releasable in nature.

While the present disclosure makes reference to certain embodiments, numerous modifications, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. An assessment system for vagus nerve stimulation therapy treatment for congestive heart failure in a subject, the assessment system comprising:
    a first interface configured to communicate with a device that delivers a stimulation signal to a vagus nerve of the subject;
    a second interface configured to capture heart electrical activity of the subject in response to the stimulation signal; and
    a processor and a non-transitory computer readable memory storing instructions that, when executed by the processor, cause the assessment system to:
        segregate the captured heart electrical activity into portions that correspond to at least one ON-period of the stimulation signal and at least one OFF-period of the stimulation signal based on a communication between the first interface and the device that delivers the stimulation signal; and
        determine and display real-time heart rate dynamics for each of the at least one ON-period and the at least one OFF-period and display a digital ECG signal in real-time in response to the stimulation signal.

2. The system of claim 1, wherein the instructions further cause the assessment system to:
    determine the real-time heart rate dynamics and display the digital ECG signal for a plurality of cycles of stimulation signal delivery, each cycle defined by an ON-period and an OFF-period of the stimulation signal; and provide an indication of autonomic engagement of the subject within 20 cycles.

3. The system of claim 2, wherein the instructions cause the assessment system to provide the indication of the autonomic engagement within 10 cycles.

4. The system of claim 3, wherein the instructions cause the assessment system to provide the indication of the autonomic engagement within 5 cycles.

5. The system of claim 4, wherein the instructions cause the assessment system to provide the indication of the autonomic engagement in real-time.

6. The system of claim 1, wherein the instructions cause the assessment system to:

record an ECG waveform signal from the captured heart electrical activity and synchronize recording of the ECG waveform signal with a timing of the stimulation signal delivery;

generate and display a plurality of QRS complexes from the ECG waveform signal;

identify a differential in the QRS complexes between ON-periods in which the stimulation signal is delivered as compared to OFF-periods in which the stimulation signal is not delivered; and display the differential as indicating autonomic engagement.

7. The system of claim 6, wherein the differential is a comparison of R-R intervals of the QRS complexes for the ON-periods as compared to the OFF-periods.

8. The system of claim 1, wherein the instructions further cause the assessment system to record and display a waveform of the digital ECG signal response in real-time from the heart electrical activity captured by the second interface; and wherein the displayed real-time heart rate dynamics include at least one of a real-time heart rate, a first average heart rate for ON-periods in which the stimulation signal is delivered, a second average heart rate for OFF-periods in which the stimulation signal is not delivered, or a difference between the second and the first average heart rates.

9. The system of claim 1, wherein the display of the real-time heart rate dynamics and the digital ECG signal can be archived and played back.

10. The system of claim 1, wherein the first interface communicates an ON-period during which stimulation is being delivered and an OFF-period during which no stimulation is being delivered; and wherein the instructions further cause the assessment system to determine and indicate the stimulation signal delivery including the ON- and OFF-periods.

11. The system of claim 1, wherein the display of the real-time heart rate dynamics and the digital ECG signal is dynamic.

12. The system of claim 11, wherein a display playback speed can be controlled.

13. A titration assessment system for vagus nerve stimulation therapy treatment in a subject, the titration assessment system comprising:

an ECG cable assembly configured to acquire an ECG signal response in the subject;

a VNS titration assembly configured to deliver a periodic stimulation signal having ON-periods and OFF-periods;

a data acquisition system coupled to the ECG cable assembly and configured to capture the ECG signal response and detect delivery of the stimulation signal; and a processor and a non-transitory computer readable memory storing instructions that, when executed by the processor, cause the titration assessment system to:

segregate the ECG signal response to the stimulation signal into portions that correspond to at least one ON-period of the ON-periods and at least one OFF-period of the OFF-periods based on the data acquisition system detecting the delivery of the stimulation signal;

process the ECG signal response to determine R-R intervals in the ECG signal response corresponding to the ON-periods and the OFF-periods;

determine and display real-time heart rate dynamics for each of the at least one ON-period and the at least one OFF-period; and digitally reproduce the ECG signal response for display.

14. The system of claim 13, wherein the VNS titration assembly includes an implantable stimulation device and a wand configured to wirelessly interface with the implantable stimulation device.

15. The system of claim 14, wherein the implantable stimulation device includes an implantable cardioverter-defibrillator (ICD).

16. A method of assessing a vagus nerve stimulation treatment for a subject comprising:

segregating an ECG signal response to the vagus nerve stimulation treatment into portions that correspond to at least one ON-period of a stimulation signal and at least one OFF-period of the stimulation signal based on a communication between a first interface and a device that delivers the stimulation signal;

determining and displaying real-time heart rate dynamics in the ECG signal response for a plurality of cycles of stimulation signal delivery, each cycle defined by an ON-period and an OFF-period of the stimulation signal;

digitally displaying the ECG signal response in real-time; and providing an indication of autonomic engagement of the subject within 20 cycles, the indication of autonomic engagement being based on the real-time heart rate dynamics for the at least one ON-period and the at least one OFF-period.

17. The method of claim 16, wherein providing the indication of the autonomic engagement comprises providing the indication of the autonomic engagement within 10 cycles.

18. The method of claim 16, wherein providing the indication of the autonomic engagement comprises providing the indication of the autonomic engagement within 5 cycles.

19. The method of claim 16, wherein providing the indication of the autonomic engagement comprises providing the indication of the autonomic engagement in real-time.

20. The method of claim 16, further comprising:

recording an ECG waveform signal from the ECG signal response and synchronizing recording of the ECG waveform signal with a timing of the stimulation signal delivery;

generating and displaying a plurality of QRS complexes from the ECG waveform signal;

identifying a differential in the QRS complexes between the ON-periods as compared to the OFF-periods; and displaying the differential as indicating autonomic engagement.

* * * * *